United States Patent [19]

Chauvin et al.

[11] Patent Number: 5,675,051
[45] Date of Patent: Oct. 7, 1997

[54] CATALYTIC COMPOSITION AND OLEFIN DISPROPORTION PROCESS

[75] Inventors: Yves Chauvin, Le Pecq; Francoise Di Marco-Van Tiggelen, Nánterre, both of France

[73] Assignee: Institut Francais Du Petrole, Rueil Malmaison, France

[21] Appl. No.: 551,338

[22] Filed: Nov. 1, 1995

Related U.S. Application Data

[62] Division of Ser. No. 377,705, Jan. 25, 1995, Pat. No. 5,525,567.

[30] Foreign Application Priority Data

Jan. 26, 1994 [FR] France ................... 94 00823

[51] Int. Cl.$^6$ .................................................. C07C 6/00
[52] U.S. Cl. ....................... 585/646; 585/643; 585/645
[58] Field of Search ................... 585/643, 645, 585/646; 502/162, 200, 210, 228, 305, 321

[56] References Cited

U.S. PATENT DOCUMENTS

| | | | |
|---|---|---|---|
| 3,691,095 | 9/1972 | Kroll et al. | 502/102 |
| 3,855,340 | 12/1974 | Knoche | 260/683 D |
| 4,550,216 | 10/1985 | Basset et al. | 585/645 |
| 4,754,099 | 6/1988 | Kemp et al. | 585/646 |
| 4,962,263 | 10/1990 | Hamilton, Jr. et al. | 585/646 |
| 5,104,840 | 4/1992 | Chauvin et al. | 502/117 |

FOREIGN PATENT DOCUMENTS

| | | |
|---|---|---|
| 129474 | 12/1984 | European Pat. Off. . |
| 283400 | 9/1988 | European Pat. Off. . |
| 448445 | 9/1991 | European Pat. Off. . |

*Primary Examiner*—Glenn A. Caldarola
*Assistant Examiner*—Thuan D. Dang
*Attorney, Agent, or Firm*—Millen, White, Zelano & Branigan, P.C.

[57] ABSTRACT

The invention concerns a catalytic olefin disproportion (also known as metathesis) process wherein the catalyst produced by dissolving a tungsten and/or molybdenum compound, more particularly a tungsten and/or molybdenum halide substituted with one or more phenoxo groups containing at least two hydrocarbon substituents in the ortho, ortho' positions, in a medium produced by mixing at least one quaternary ammonium halide and/or at least one quaternary phosphonium halide, at least one aluminium halide, and an organometallic aluminium compound.

21 Claims, No Drawings

CATALYTIC COMPOSITION AND OLEFIN DISPROPORTION PROCESS

This is a division of the application Ser. No. 08/377,705 filed Jan. 25, 1995 now the U.S. Pat. No. 5,525,567.

BACKGROUND OF THE INVENTION

The present invention concerns a catalytic process for the disproportion (also known as metathesis) of olefins. This catalyst is produced by dissolving a tungsten and/or molybdenum compound in an ionic liquid mixture of a quaternary ammonium halide and/or a quaternary phosphonium halide, an aluminium halide, and an aluminium alkyl compound.

Olefin disproportionation is readily catalysed by typically heterogeneous catalysts such as molybdenum, tungsten or rhenium oxides deposited on silica or alumina, or by organometallic catalysts known as homogeneous catalysts, produced by combining halides or substituted halides of tungsten and molybdenum with organometallic compounds from the principal series, more particularly organic aluminium compounds. Different organometallic systems have been described by H T Dodd and K J Rutt in Journal of Molecular Catalysis, 15, 1982, pp103–110.

More recently, J M Basset et al, in U.S. Pat. No. 4,550,216, have shown that in a chlorobenzene medium, the product of the interaction of a halogenated tungsten compound containing two phenoxo groups which are themselves substituted by electronegative groups in the ortho positions, with organometallic compounds from the principal series was particularly active in olefin metathesis catalysis. The problem with the system, however, was that it was not possible to exploit the full capabilities of the catalyst before its destruction.

U.S. Pat. No. 5,104,840 describes a liquid composition of ionic character produced by bringing quaternary ammonium halides and/or quaternary phosphonium halides into contact with alkyl aluminium dihalides and, optionally, an aluminium trihalide. This patent describes the use of these media as solvents for transition metal complexes, in particular nickel complexes which do not contain a carbon-nickel bond, which are transformed into olefin oligomerisation catalysts. The use of such media, which are not miscible with aliphatic hydrocarbons, in particular with the products of olefin transformation, results in better separation of the products and improves the use of homogeneous catalysts. In the following description, these media are termed "molten salts" since they are liquid at moderate temperatures.

We have now discovered that tungsten or molybdenum halides substituted with one or two phenoxo groups containing at least two hydrocarbon substituents in the ortho, ortho' positions, when dissolved in "molten salts", are effective olefin disproportion catalysts. This formulation has proved to be of particular interest since the tungsten or molybdenum complexes dissolved therein are insoluble in olefins, have a high catalytic activity and can be used over the whole of the active period.

SUMMARY OF THE INVENTION

More precisely, the invention provides a catalytic composition comprising at least one tungsten or molybdenum compound, more particularly a tungsten or molybdenum halide substituted with one or two phenoxo groups which are themselves substituted in the ortho, ortho' positions with two hydrocarbon groups, at least partially dissolved in a non aqueous ionic medium produced by bringing a quaternary ammonium halide and/or at least one quaternary phosphonium halide (termed product A) into contact with at least one aluminium halide (termed product B) and with at least one organometallic aluminium compound (termed product C).

A further object of the invention is to provide a process for the disproportionation or codisproportionation of at least one olefin, wherein the olefin is brought into contact with at least one tungsten or molybdenum compound, said compound being at least partially dissolved in a non aqueous ionic medium, said medium being produced by bringing at least one aluminium halide into contact with at least one quaternary ammonium halide and/or quaternary phosphonium halide and with an organometallic aluminium derivative.

The "molten salt" medium is thus constituted by:

a) halides, more particularly chlorides and/or bromides, of quaternary ammonium and/or quaternary phosphonium compounds (termed product A);

b) an aluminium halide, more particularly aluminium chloride or bromide (termed product B);

c) an organic aluminium derivative (termed product C).

Suitable quaternary ammonium halides and quaternary phosphonium halides preferably have general formulae $NR^1R^2R^3R^4X$ and $PR^1R^2R^3R^4X$, where X represents Cl or Br, $R^1$, $R^2$, $R^3$ and $R^4$, which may be identical or different, each represent hydrogen, an alkyl group, a saturated or unsaturated aliphatic group or an aromatic group, containing 1 to 12 carbon atoms. The quaternary ammonium and/or phosphonium halides can also be constituted by heterocyclic derivatives containing 1, 2 or 3 nitrogen and/or phosphorus atoms. Radicals such as $R^6$ can also connect two molecules as defined above, for example in $R^1R^2N^+=CR_3-R^6-CR_3=N^+R^1R^2(X^-)_2$; $R^6$ may be an alkylene or phenylene residue. Examples are tetrabutylphosphonium chloride, N-butylpyridinium chloride, ethyl pyridinium bromide, 3-butyl-1-methylimidazolium chloride, diethylpyrazolium chloride, pyridinium hydrochloride, and trimethylphenyl ammonium chloride.

The organic aluminium derivatives of the invention have the general formula $AlR_xX_{3-x}$ where R is a linear or branched alkyl radical containing 2 to 8 carbon atoms, X is chlorine or bromine and x is equal to 1, 2 or 3. Examples are dichloroethylaluminium, ethylaluminium sesquichloride, isobutylaluminium sesquichloride, dichloroisobutylaluminium and chlorodiethylaluminium.

The "molten salt" components defined above are used in molar ratios A:B of between 1:0.5 and 1:3, preferably between 1:0.8 and 1:2; B:C is between 1:0.01 and 1:1.5, preferably between 1:0.01 and 1:1. The components and their proportions must, however, be selected so that the mixture is liquid at the temperature at which the tungsten or molybdenum compound is introduced, even if the catalytic disproportionation reaction can be carried out at a temperature which is above or below the melting temperature of the catalytic composition.

The compounds in the composition of the invention can be mixed in any order. Mixing can be effected simply by bringing them into contact followed by agitation to form a homogeneous liquid. Mixing can be carried out outside the disproportion reactor or, preferably, in the reactor.

The tungsten compounds of the invention have the general formula $WX_{6-x}(OAr)_x$ and the molybdenum compounds of the invention have the general formula $MoX_{5-x}(OAr)_x$ where X represents chlorine or bromine and Ar represents an aromatic group containing at least two hydrocarbon substituents in the ortho, ortho' positions, and x equals 1 or 2. The aromatic group is preferably a phenyl group, and the substituents are phenyl, alkyl or cycloalkyl groups, for example methyl, isopropyl, tertiobutyl or cyclohexyl.

Examples of tungsten or molybdenum compounds which are suitable for use in the present invention are the following complexes: $WCl_4[O-2,6-C_6H_3(C_6H_5)_2]_2$, $WCl_4[O-2,4,6-C_6H_2(C_6H_5)_3]_2$, $WCl_5[O-2,6-C_6H_3(C_6H_5)_2]$, $WCl_4[O-2,6-C_6H_3(C_4H_9)_2]_2$, and $MoCl_3[O-2,6-C_6H_3(C_6H_5)_2]_2$.

The concentration of the tungsten or molybdenum compound in the "molten salt" is advantageously between 5 and 200 mmol per liter, preferably between 10 and 100 mmol per liter.

Olefins which can be transformed by catalytic compositions of the invention are propylene, n-butenes and n-pentenes, alone or in a mixture, pure or diluted by an alkane, as is the case for cuts from petroleum refining processes, such as catalytic cracking or steam cracking.

Catalytic disproportionation of olefins can be carried out in a batch process, a semi-continuous process or a continuous process comprising one or more reaction stages. Vigorous agitation is essential to ensure good contact between the reactant(s) and the catalytic composition. The reaction temperature can be between −40° C., and +70° C., preferably between −20° C. and +50° C. The operation can be carried out at a temperature above or below the melting temperature of the catalytic composition, as the dispersed solid state does not impede the reaction. The pressure can be between atmospheric pressure and 20 MPa, preferably between atmospheric pressure and 5 MPa. The reaction products are separated from the catalytic system by simple decantation followed by fractionation.

The following examples illustrate the invention without limiting its scope.

EXAMPLE 1

Ionic solvent preparation 17.5 g (0.1 mole) of butylmethyl imidazolium chloride was mixed with 12.8 g (0.096 mole) of sublimed aluminium chloride at room temperature (molar fraction of aluminium chloride: 0.489).

Disproportionation of 2-pentene

A 100 ml glass reactor, provided with a magnetic bar stirrer to ensure adequate stirring and a double envelope for circulation of a temperature regulation liquid, was purged of air and moisture and kept in an argon atmosphere. 83 mg (0.1 mmole) of $WCl_4[O-2,6-C_6H_3(C_6H_5)_2]_2$ complex was introduced at 30° C., and 4.4 g of the liquid composition prepared above, plus 8 ml of heptane containing 0.245 g (1.9 mmole) of dichloroethylaluminium were injected using a syringe, followed by 10 ml of 2-pentene. Stirring was commenced and after 4 hours, the "molten salt" was decanted off and most of the hydrocarbon phase was extracted. This operation was carried out twice. By this time, a total of 20 ml of olefins had been introduced. Analysis showed that the mixture contained 25 molar % of 2-butene, 25 molar % of 3-hexene and 50 molar % of 2-pentene, i.e., thermodynamic equilibrium of the disproportionation reaction had been achieved. The operation was repeated several times.

EXAMPLE 2

Ionic solvent preparation 17.5 g (0.1 mole) of butylmethyl imidazolium chloride was mixed with 16.02 g (0.12 mole) of sublimed aluminium chloride at room temperature (molar fraction of aluminium chloride: 0.545).

Disproportion of 2-pentene

The method of Example 1 was followed, with the exception that 107 mg of $WCl_4[O-2,6-C_6H_3(C_6H_5)_2]_2$ complex, 4 g of the prepared molten salt and 0.4 g (3.2 mmole) of dichloroethylaluminium were introduced. Analysis showed that 2 successive charges of 2-pentene produced thermodynamic equilibrium.

EXAMPLE 3

Disproportion of 2-pentene

The method of Example 2 was followed, with the exception that 122 mg (0.13 mmole) of $WCl_4[O-2,4,6-C_6H_2(C_6H_5)_3]$ complex and 0.4 g (3.2 mmole) of dichloroethylaluminium were introduced. Analysis showed that 2 successive charges of 2-pentene produced thermodynamic equilibrium.

EXAMPLE 4

Disproportion of 2-pentene

The method of Example 1 was followed, with the exception that 72 mg (0.07 mmole) of $WCl_4[O-2,4,6-C_6H_2(C_6H_5)_3]_2$ complex and 0.49 g (3.9 mmole) of dichloroethylaluminium were introduced. The result was identical to that of Example 1.

EXAMPLE 5

Ionic solvent preparation 17.5 g (0.1 mole) Of butylmethyl imidazolium chloride was mixed with 11.9 g (0.086 mole) of sublimed aluminium chloride at room temperature (molar fraction of aluminium chloride: 0.47).

Disproportion of 2-pentene

The method of Example 1 was followed, with the exception that 62 mg (0.1 mmole) of $WCl_5[O-2,6-C_6H_3(C_6H_5)_2]$ complex, 3.25 g of the prepared molten salt and 0.245 g (1.9 mmole) of dichloroethylaluminium were introduced. After 4 hours, 33% had been converted.

EXAMPLE 6

Disproportion of 2-pentene

The method of Example 1 was followed, with the exception that 100 mg (0.14 mmole) of $WCl_4[O-2,4,6-C_6H_3(C_4H_9)_2]_2$ complex and 0.49 g (3.9 mmole) of dichloroethylaluminium were introduced. After 4 hours, 40% had been converted.

EXAMPLE 7

Disproportion of 2-pentene

The method of Example 6 was followed, with the exception that 100 mg (0.14 mmole) of $MoCl_3[O-2,6-C_6H_3(C_6H_5)_2]_2$ complex and 0.49 g (3.9 mmole) of dichloroethylaluminium were introduced. After 4 hours, 40% had been converted.

We claim:

1. A catalytic process for disproportion or codisproportion of at least one olefin, comprising contacting the olefin with at least one tungsten or molybdenum compound, said compound being at least partially dissolved in an ionic non aqueous medium, said medium having been produced by a process comprising bringing at least one aluminum halide (A) into contact with at least one quaternary ammonium halide and/or at least one quaternary phosphonium halide (B) and with at least one organometallic aluminum compound (C).

2. A catalyst process according to claim 1, said reaction with the olefin being conducted at a reaction temperature between −40° C. and +70° C., and a pressure between 0.1 and 20 MPa.

3. A process according to claim 1, wherein the reaction with the olefin is carried out at a temperature of between −20° C. and +30° C.

4. A catalytic process according to claim 1, said medium having been produced with a quaternary ammonium halide selected from the group consisting of by N-butylpyridinium chloride, ethylpyridinium bromide, 3-butyl-1-methyl imidazolium chloride, diethylpyrazolium chloride, pyridinium hydrochloride and trimethylphenyl ammonium chloride.

5. A catalytic process according to claim 1, said medium having been produced with a quaternary phosphonium halide.

6. A catalytic process according to claim 5, wherein the quaternary phosphonium halide is tetrabutylphosphonium chloride.

7. A catalytic process according to claim 1, wherein the aluminum halide is selected from the group consisting of aluminum chloride and aluminum bromide.

8. A catalytic process according to claim 4, wherein the aluminum halide is selected from the group consisting of aluminum chloride and aluminum bromide.

9. A catalytic process according to claim 6, wherein the aluminum halide is selected from the group consisting of aluminum chloride and aluminum bromide.

10. A catalytic process according to claim 1, wherein the organometallic aluminum compound (C) is of the general formula $AlR_xX_{3-x}$ where R is a linear or branched alkyl radical containing 2 to 8 carbon atoms, X is chlorine or bromine and X equals 1, 2 or 3.

11. A catalytic process according to claim 4, wherein the organometallic aluminum compound (C) is of the general formula $AlR_xX_{3-x}$ where R is a linear or branched alkyl radical containing 2 to 8 carbon atoms, X is chlorine or bromine and X equals 1, 2 or 3.

12. A catalytic process according to claim 6, wherein the organometallic aluminum compound (C) is of the general formula $AlR_xX_{3-x}$ where R is a linear or branched alkyl radical containing 2 to 8 carbon atoms, X is chlorine or bromine and X equals 1, 2 or 3.

13. A catalytic process according to claim 3, wherein the organometallic aluminum compound (C) is of the general formula $AlR_xX_{3-x}$ where R is a linear or branched alkyl radical containing 2 to 8 carbon atoms, X is chlorine or bromine and X equals 1, 2 or 3.

14. A catalytic process according to claim 10, wherein the organometallic aluminum compound is selected from the group consisting of dichloroethylaluminium, dichloroisobutylaluminum, chlorodiethylaluminum, ethylaluminum sesquichloride and isobutylaluminium sesquichloride.

15. A catalytic process according to claim 1, having a molar ratio B:A between 1:0.5 and 1:3, and a molar ratio A:C between 1:0.1 and 1:1.:5.

16. A catalytic process according to claim 1, having a molar ratio B:A between 1:0.8 and 1:2 and a molar ratio A:C between 1:0.1 and 1:1.

17. A catalytic process according to claim 1, wherein the process is conducted in contact with a tungsten compound of the formula $WX_{6-x}(OAr)_x$, wherein X represents chlorine or bromine and Ar represents an aromatic group containing at least two hydrocarbon substituents in the ortho, ortho' positions, and x equals 1 or 2.

18. A catalytic process according to claim 13, wherein the process is conducted in contact with a tungsten compound of the formula $WX_{6-x}(OAr)_x$, wherein X represents chlorine or bromine and Ar represents an aromatic group containing at least two hydrocarbon substituents in the ortho, ortho' positions, and x equals 1 or 2.

19. A catalytic process according to claim 1, wherein the process is conducted in contact with a molybdenum compound of the formula $MoX_{5-x}(OAr)_x$, wherein X represents chlorine or bromine and Ar represents an aromatic group containing at least two hydrocarbon substituents in the ortho, ortho' positions, and x equals 1 or 2.

20. A catalytic process according to claim 13, wherein the process is conducted in contact with a molybdenum compound of the formula $MoX_{5-x}(OAr)_x$, wherein X represents chlorine or bromine and Ar represents an aromatic group containing at least two hydrocarbon substituents in the ortho, ortho' positions, and x equals 1 or 2.

21. A catalytic process according to claim 1, wherein component (b) is at least one quaternary ammonium halide.

* * * * *